United States Patent [19]

Radunz et al.

[11] 4,309,441
[45] Jan. 5, 1982

[54] 13-THIAPROSTAGLANDIN DERIVATIVES

[75] Inventors: Hans-Eckart Radunz; Dieter Orth; Manfred Baumgarth; Hans-Jochen Schliep; Hans-Joachim Enenkel, all of Darmstadt, Fed. Rep. of Germany

[73] Assignee: Merck Patent Gesellschaft mit beschrankter Haftung, Darmstadt, Fed. Rep. of Germany

[21] Appl. No.: 96,348

[22] Filed: Nov. 21, 1979

Related U.S. Application Data

[63] Continuation-in-part of Ser. No. 837,975, Sep. 29, 1977.

[30] Foreign Application Priority Data

Oct. 6, 1976 [DE] Fed. Rep. of Germany ....... 2644972

[51] Int. Cl.³ ................. C07C 177/00; A61K 31/557
[52] U.S. Cl. ................................ 424/305; 424/308; 560/9; 560/121
[58] Field of Search ................. 560/121, 9; 424/305, 424/308

[56] References Cited

U.S. PATENT DOCUMENTS

| | | | |
|---|---|---|---|
| 3,894,062 | 7/1975 | Morozowich | 560/121 |
| 3,931,285 | 1/1976 | Morozowich | 560/121 |
| 3,932,486 | 1/1976 | Morozowich | 560/121 |
| 3,932,487 | 1/1976 | Kramer et al. | 260/468 D |
| 3,994,956 | 11/1976 | Morozowich | 560/121 |
| 3,998,869 | 12/1976 | Morozowich | 560/121 |
| 4,080,458 | 3/1978 | Radunz et al. | 560/121 |

*Primary Examiner*—Robert Gerstl
*Attorney, Agent, or Firm*—Millen & White

[57] ABSTRACT

13-Thiaprostanoic acid derivatives of the general formula I

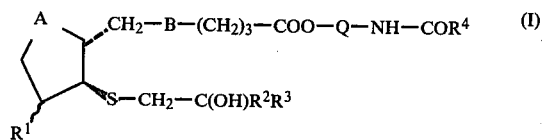

wherein A is —CO— or —CHOH—; B is —CH$_2$CH$_2$— or —CH=CH—; Q is 1,4-phenylene or 1,4-naphthylene; $R^1$ is H or OH; $R^2$ is H or CH$_3$; $R^3$ is alkyl with 1–8 carbon atoms or alkyl with 1–8 carbon atoms substituted by (a) phenyl, (b) phenyl substituted by at least one of CH$_3$, F, Cl, Br, OH, OCH$_3$ or CF$_3$; (c) phenoxy or (d) phenoxy substituted by at least one of CH$_3$, F, Cl, Br, OH, OCH$_3$ or CF$_3$; and $R^4$ is NH$_2$, CH$_3$, phenyl, p-acetylaminophenyl, p-benzoylaminophenyl or phenylamino. These compounds are useful for lowering blood pressure as well as for other pharmaceutical purposes. They also are useful intermediates for the preparation of other known pharmaceuticals such s the 13-thiaprostaglandins.

11 Claims, No Drawings

13-THIAPROSTAGLANDIN DERIVATIVES

CROSS-REFERENCE TO RELATED APPLICATIONS

This application is a continuation-in-part application of copending United States application Ser. No. 837,975, filed on Sept. 29, 1977.

BACKGROUND OF THE INVENTION

The present invention relates to new compounds which are pharmaceutically active, e.g., as blood pressure reducers, and which in particular, can be used as intermediates in the preparation of other pharmaceuticals, e.g., the 13-thiaprostaglandins.

SUMMARY OF THE INVENTION

In a composition aspect, the present invention provides 13-thiaprostanoic acid derivatives of the general formula I

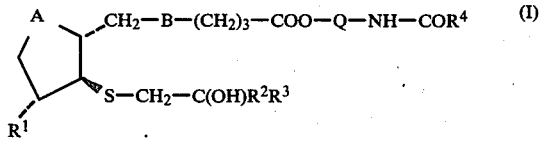

wherein A is —CO— or —CHOH—; B is —CH$_2$CH$_2$— or —CH=CH—; Q is 1,4-phenylene or 1,4-naphthylene; R$^1$ is H or OH; R$^2$ is H or CH$_3$; R$^3$ is alkyl with 1–8 carbon atoms or alkyl with 1–8 carbon atoms substituted by (a) phenyl, (b) phenyl substituted by at least one of CH$_3$, F, Cl, Br, OH, OCH$_3$ or CF$_3$; (c) phenoxy or (d) phenoxy substituted by at least one of CH$_3$, F, Cl, Br, OH, OCH$_3$ or CF$_3$; and R$^4$ is NH$_2$, CH$_3$, phenyl, p-acetylaminophenyl, p-benzoylaminophenyl or phenylamino. These compounds are useful for lowering blood pressure as well as for other pharmaceutical purposes. They also are useful intermediates for the preparation of other known pharmaceuticals such as the 13-thiaprostaglandins of formula VI herein.

In another composition aspect, this invention involves compositions of the compounds of formula I with pharmaceutically acceptable carriers and/or adjuvants.

In a method of use aspect, this invention provides a method for lowering blood pressure in mammals which comprises administering an amount of a compound of formula I effective for lowering blood pressure.

Upon further study of the specification and appended claims, further objects and advantages of this invention will become apparent to those skilled in the art.

DETAILED DISCUSSION

The compounds of formula I are structurally related to the prostaglandins which are derived from 1-(2-octylcyclopentyl)-heptanoic acid (prostanoic acid), and can be characterized as derivatives of 13-thiaprostanoic acid. (See also U.S. Pat. No. 3,932,487).

In formula I and the other formulae of this application, an α-bond is shown dotted and a β-bond is thickly drawn. Bonds which are in the α- or β-configuration are characterized by a wavy line.

The compounds of formula I contain at least 3 asymmetrical carbon atoms on the five-membered ring. When A is —CHOH—, then four asymmetric centers are present in the ring. In the thioether side chain, further asymmetric centers can occur. Therefore, the compounds of formula I can appear in a multiplicity of stereoisomeric forms; as a rule, they are present as racemic mixtures. This invention includes the optically-active isomers of the formula I in addition to the individual racemates and racemic mixtures.

When A is a —CHOH— group, the OH group can be in the α- or β-position.

When B is a 1,2-vinylene radical, it is preferably cis-substituted.

In the above formulae, R$^1$ is, in addition to hydrogen, especially also OH.

R$^2$ is H or CH$_3$.

When R$^3$ is alkyl with 1 to 8 carbon atoms, it preferably is unbranched, and especially contains 4 to 7 carbon atoms, such as butyl, pentyl, hexyl or heptyl. Methyl, ethyl, propyl or octyl are also included.

When R$^3$ is branched alkyl, it preferably contains 5 to 7 carbon atoms, such as 1-methylbutyl, 1-methylpentyl, 1-methylhexyl, 1,1-dimethylbutyl, 1,1-dimethylpentyl, 4-methylpentyl or 4,4-dimethylpentyl. However, other branched radicals are also included, such as isopropyl, isobutyl, tert-butyl, isopentyl, neopentyl, 1-methylheptyl or 1,1-dimethylhexyl.

R$^3$ can also be alkyl with 1–8 carbon atoms, preferably with 1 or 2 carbon atoms, substituted by phenyl or phenoxy, or by phenyl or phenoxy either of which in turn is substituted by CH$_3$, F, Cl, Br, OH, OCH$_3$ or CF$_3$. Singly substituted phenyl or phenoxy radicals are preferred, especially when they are substituted in the m- or p-position. Especially preferred such substituted radicals include: p-tolyl, p-tolyloxy, p-fluorophenyl, p-fluorophenoxy, p-chlorophenyl, p-chlorophenoxy, m-chlorophenyl, m-chlorophenoxy, m-bromophenyl, m-bromophenoxy, p-hydroxyphenyl, p-hydroxyphenoxy, m-hydroxyphenyl, m-hydroxyphenoxy, p-methoxyphenyl, p-methoxyphenoxy, m-methoxyphenyl, m-methoxyphenoxy, m-trifluoromethylphenyl or m-trifluoromethylphenoxy. Other monosubstituted radicals are also included, e.g., m-tolyl, m-tolyloxy, o-fluorophenyl, o-fluorophenoxy, m-fluorophenyl, m-fluorophenoxy, o-chlorophenyl, o-chlorophenoxy, p-bromophenyl, p-bromophenoxy, p-trifluoromethylphenyl and p-trifluoromethylphenoxy. Phenyl and phenoxy may also be multi-substituted. In addition to the disubstituted versions, 2,4,6-trimethylphenyl, 2,4,6-trimethylphenoxy, 3,4,5-trimethoxyphenyl and 3,4,5-trimethoxyphenoxy are especially preferred. The disubstituted radicals preferably contain two identical substituents, e.g., 2,4-dichlorophenyl, 2,4-dichlorophenoxy, 2,4-dibromophenyl, 2,4-dibromophenoxy, 2,4-dimethylphenyl, 2,4-dimethylphenoxy, 2,4-dihydroxyphenyl, 2,4-dihydroxyphenoxy, 3,4-dihydroxyphenyl, 3,4-dihydroxyphenoxy, 2,4-dimethoxyphenyl, and 2,4-dimethoxyphenoxy. However, such radical can also be unsymmetrically substituted, e.g., 3-chloro-4-methylphenyl, 3-chloro-4-methylphenoxy, 3-fluoro-4-methylphenyl, 3-fluoro-4-methylphenoxy, 3-chloro-4-methoxyphenyl or 3-chloro-4-methoxyphenoxy.

When R$^3$ is an alkyl radical with 1–8 carbon atoms, preferably with 1 or 2 carbon atoms, substituted as defined above, the following R$^3$ radicals are especially preferred: p-tolylmethyl, 2-p-tolylethyl, p-fluorophenylmethyl, 2-p-fluorophenylethyl, p-chlorophenylmethyl, 2-p-chlorophenylethyl, m-chlorophenylmethyl, 2-m-chlorophenylethyl, m-methoxyphenylmethyl, 2-m-methoxyphenylethyl, m-trifluoromethylphenylmethyl, 2-m-trifluoromethylphenylethyl, p-tolyloxymethyl, p-fluorophenoxymethyl, p-chlorophenoxymethyl, m-chlorophenoxymethyl, m-methoxyphenoxymethyl and m-trifluoromethylphenoxymethyl.

Q is preferably 1,4-phenylene but can also be 1,4-naphthylene.

$R^4$ is preferably methyl, $NH_2$, 4-acetylaminophenyl and especially phenyl.

Contemplated classes of compounds within the scope of formula I are those wherein:
(a) A is —CO—;
(b) A is —CHOH—;
(c) B is —$CH_2CH_2$—, including each of those of a and b;
(d) B is —CH=CH—, including each of those of a and b;
(e) Q is 1,4-phenylene, including each of those of a–d;
(f) Q is 1,4-naphthylene, including each of those of a–d;
(g) $R^1$ is H, including each of those of a–f;
(h) $R^1$ is OH, including each of those of a–f;
(i) $R^2$ is H or $CH_3$, including each of those of a–h;
(j) $R^3$ is $C_{1-8}$ alkyl, including each of those of a–i;
(k) $R^3$ is $C_{1-8}$ alkyl substituted by phenyl, including each of those of a–i;
(l) $R^3$ is $C_{1-8}$ alkyl substituted by phenoxy, including each of those of a–i;
(m) $R^3$ is $C_{1-8}$ alkyl substituted by phenyl which is substituted by $CH_3$, F, Cl, Br or $CF_3$, including each of those of a–i;
(n) $R^3$ is $C_{1-8}$ alkyl substituted by phenyl which is substituted by OH or $OCH_3$, including each of those of a–i;
(o) $R^3$ is $C_{1-8}$ alkyl substituted by phenoxy which is substituted by $CH_3$, F, Cl, Br or $CF_3$, including each of those of a–i;
(p) $R^3$ is $C_{1-8}$ alkyl substituted by phenoxy which is substituted by OH or $OCH_3$, including each of those of a–i;
(q) $R^4$ is $CH_3$ or phenyl, including each of those of a–p;
(r) $R^4$ is $NH_2$, or phenylamino, including each of those of a–p;
(s) $R^4$ is p-acetylaminophenyl or p-benzoylaminophenyl, including each of those of a–p.

Especially preferred are those compounds of formula I in which at least one of $R^1$, $R^2$, $R^3$, $R^4$, A, B and Q are one of the embodiments described above as being preferred. Some of these preferred groups of compounds can be characterized by the following partial formulae Ia to Ik which otherwise correspond to formula I, and in which the symbols not more narrowly defined below have the meaning given in formula I. These groups are:
Ia: $R^1$=OH;
Ib: $R^1$=OH and B=—$CH_2$—$CH_2$—;
Ic: $R^1$=OH and B=cis—CH=CH—;
Id: $R^1$=OH, B=—$CH_2CH_2$— and $R^3$=pentyl, 1-methylpentyl or 1,1-dimethylpentyl;
Ie: $R^1$=OH, B=—$CH_2$—$CH_2$—, Q=1,4-phenylene, $R^3$=pentyl, 1-methylpentyl or 1,1-dimethylpentyl and $R^4$=phenyl;
If: $R^1$=OH, B=cis—CH=CH— and $R^3$=pentyl, 1-methylpentyl or 1,1-dimethylpentyl;
Ig: $R^1$=OH, B=cis—CH=CH—, Q=1,4-phenylene, $R^3$=pentyl, 1-methylpentyl or 1,1-dimethylpentyl and $R^4$=phenyl;
Ih: $R^1$=OH, B=—$CH_2$—$CH_2$— and $R^3$=2-phenylethyl, 2-m-chlorophenylethyl, 2-m-trifluoromethylphenylethyl, phenoxymethyl, m-chlorophenoxymethyl, m-trifluoromethylphenoxymethyl or m-methoxyphenoxymethyl;

Ii: $R^1$=OH, B=—$CH_2CH_2$—, Q=1,4-phenylene, $R^3$=2-phenylethyl, 2-m-chlorophenylethyl, 2-m-trifluoromethylphenylethyl, phenoxymethyl, m-chlorophenoxymethyl, m-trifluoromethylphenoxymethyl or m-methoxyphenoxymethyl and $R^4$=phenyl;
Ij: $R^1$=OH, B=cis—CH=CH— and $R^3$=phenylethyl, 2-m-chlorophenylethyl, 2-m-trifluoromethylphenylethyl, phenoxymethyl, m-chlorophenoxymethyl, m-trifluoromethylphenoxymethyl or m-methoxyphenoxymethyl;
Ik: $R^1$=OH, B=cis—CH=CH—, Q=1,4-phenylene, $R^3$=2-phenylethyl, 2-m-chlorophenylethyl, 2-m-trifluoromethylphenylethyl, phenoxymethyl, m-chlorophenoxymethyl, m-trifluoromethylphenoxymethyl or m-methoxyphenoxymethyl and $R^4$=phenyl.

The compounds of formula I can be prepared by processes highly analogous to known processes. Moreover, the starting materials for these processes are either themselves known or can also be prepared by processes which are analogous to conventional processes. Suitable reaction conditions can be determined from the standard works of preparative organic chemistry, e.g., HOUBEN-WEYL, *Methoden der organischen Chemie*, Georg Thieme Verlag, Stuttgart, or *Organic Syntheses*, J. Wiley, New York-London-Sydney.

One process for the preparation of the compounds of the formula I comprises reacting a compound of the formula II

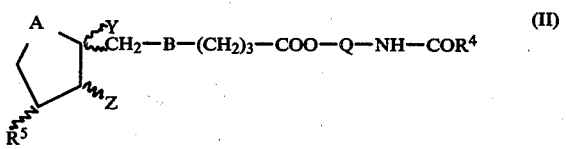

wherein $R^5$ is $R^1$ (if Z is a nucleophilic group and Y is hydrogen, or Z and Y together form an additional bond) or is an oxygen atom which also serves as Z (if Y is hydrogen); Z is a nucleophilic group, or together with Y forms an additional bond (if $R^5$ is $R^1$), or is the same oxygen atom as $R^5$ is (if Y is hydrogen); and Y signifies a hydrogen atom, or (if $R^5$=$R^1$) together with Z is an additional bond; and A, B, Q, $R^1$ and $R^4$ are defined above; with a compound of the formula III

MS—$CH_2$—C(OH)$R^2R^3$ (III)

wherein M is H, an alkali metal or alkaline earth metal atom or equivalents thereof, or ammonium, and $R^2$ and $R^3$ are as defined above.

A second process involves reacting a compound of the formula IV

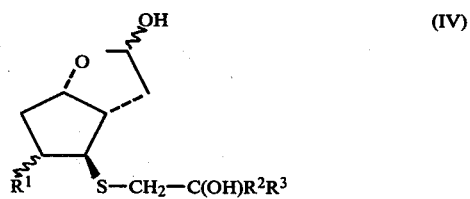

wherein $R^1$, $R^2$ and $R^3$ are defined above, with a compound of the general formula V

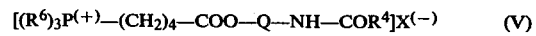

$[(R^6)_3P^{(+)}$—$(CH_2)_4$—COO—Q—NH—$COR^4]X^{(-)}$ (V)

wherein $R^6$ is alkyl with 1–4 carbon atoms or phenyl, X is Cl, Br or I and Q and $R^4$ are defined above.

In a third process, a compound of the general formula VI

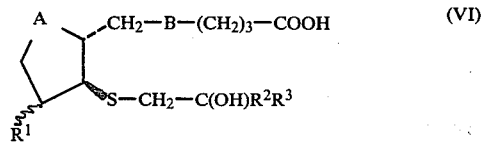

wherein A, B, $R^1$, $R^2$ and $R^3$ are defined above, or one of its reactive acid derivatives is reacted with a compound of the formula VII

wherein Q and $R^4$ are defined above.

A fourth process involves reacting a compound which otherwise corresponds to formula I but in which at least one hydroxyl group and/or carbonyl group is present in functionally changed form, with a solvolyzing agent.

In a fifth process, a compound of the formula I (A=—CO—), by reaction with a reducing agent, is converted into another compound of the general formula I (A=—CHOH—).

The compounds of formula II are new. The residues A, B, Q and $R^4$ are as defined for formula I, especially the preferred meanings. Z preferably forms, together with Y, an additional C—C bond, whereby $R^5$ then is hydrogen or OH. However, Z can also be a nucleophilic group, whereby $R^5$ is then hydrogen or OH and Y is hydrogen. Suitable nucleophilic groups include, in particular, chlorine, bromine, iodine and reactive OH groups, e.g., those esterified with sulphonic acids, e.g. alkylsulphonyloxy groups with 1–4 carbon atoms, especially methylsulphonyloxy or ethylsulphonyloxy groups; or arylsulphonyloxy groups with 6–10 carbon atoms, especially phenylsulphonyloxy, p-tolylsulphonyloxy, p-bromophenylsulphonyloxy, α-naphthylsulphonyloxy or β-naphthylsulphonyloxy groups. Furthermore, Z and $R^5$ can also be the same oxygen atom. In this case, Y must be hydrogen.

Therefore, suitable starting compounds of formula II include the compounds of the formula IIa

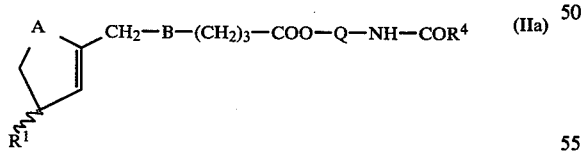

wherein A, B, Q, $R^1$ and $R^4$ are as defined above, of formula IIb

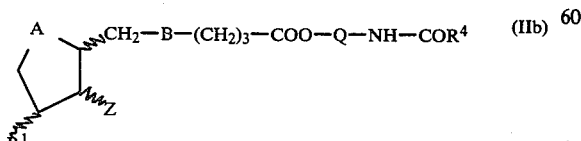

wherein Z is a nucleophilic group and A, B, Q, $R^1$ and $R^4$ are as defined above, and of formula IIc

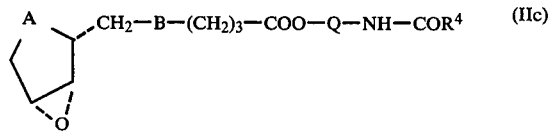

wherein A, B, Q and $R^4$ are as defined above.

These compounds of formulae IIa to IIc with Q=1,4-phenylene and $R^4$=phenyl are preferred.

It is especially advantageous to use the compounds of formula IIa as starting compounds for the preparation of the compounds of formula I.

The compounds of formula II are prepared by reaction of compounds of the formula VIII

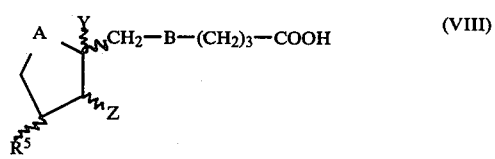

wherein A, B, Q, Z and $R^5$ are as defined previously, or of their reactive acid derivatives, with compounds of formula VII. Suitable reactive acid derivatives of the compounds of formula VIII, include the acid halides, especially the chlorides and the bromides; reactive esters, such as phenacyl esters; and, in particular, mixed anhydrides, especially with carbonic acid hemiesters, e.g. carbonic acid monoalkyl esters with 2–6 carbon atoms, such as carbonic acid monoethyl, carbonic acid monoisobutyl, carbonic acid mono-sec-butyl, carbonic acid monopentyl or carbonic acid monoisopentyl esters. The mixed anhydrides of the compounds of formula VIII with carbonic acid monoalkyl esters can be prepared according to very conventional methods by reaction of the free acids of formula VIII with chloroformic acid alkyl esters, advantageously in the presence of an organic base, such as triethylamine, under the reaction conditions conventional for such reactions. (Cf. e.g., Fieser, Fieser, *Reagents for Organic Synthesis,* page 86, New York-London-Syndey 1967).

The most important compounds of formula VIII are those of formula VIIIa

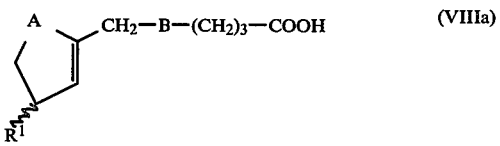

wherein A, B and $R^1$ are defined above.

In addition, the compounds of formula VIIIb

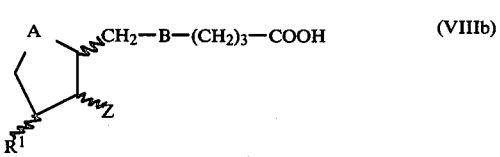

wherein Z is a nucleophilic group and A, B and $R^1$ are defined above, and the compounds of formula VIIIc

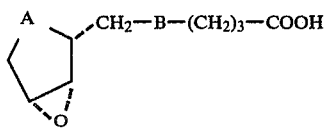

(VIIIc)

wherein A and B are defined above, are also to be regarded as important starting materials.

The compounds of formula VIII are, in part, known and in part, new. The new compounds of formula VIII can be prepared by analogy to the known compounds of formula VIII according to standard methods known from the literature using known preproducts. It is, for example, also possible to prepare compounds of formula VIIIa with A=—CHOH from the well-known compounds of the formula VIIIa with A=—CO— in analogy to, for example, the process described in J. Organic Chem. 40, 1864 (1975) by reduction with, e.g., aluminum hydrides, such as AlH$_3$ or (C$_4$H$_9$)$_2$AlH.

The reaction of a compound of formula VIII or of one of its acid derivatives with a compound of formula VII is conducted according to well known conventional methods. If the free acids of formula VIII are used, it is advantageous to employ a water-binding agent, e.g., a carbodiimide, such as dicyclohexyl carbodiimide, and an inert organic solvent, preferably an ether, such as diethyl ether, 1,2-dimethoxyethane, tetrahydrofuran (=THF) or dioxane; or a halogenated hydrocarbon, such as methylene chloride or 1,2-dichloroethane. Reaction conditions which are suitable for this reaction are known and are described, e.g., in Tetrahedron, 21, 3531 (1965); the reaction temperatures lie, for example, approximately between 20° and 100° C.

If one uses a reactive acid derivative of a compound of formula VIII for the preparation of a compound of formula II, the mixed anhydrides with carbonic acid hemiesters, especially with carbonic acid monoisobutyl ester, are particularly suitable. The mixed anhydrides are preferably not isolated after their preparation but rather are brought to reaction in situ with the compounds of formula VII. As a rule, temperatures between about 10° C. and about 40° C. are employed, preferably room temperature, along with the use of an inert organic solvent. Suitable solvents include ketones, preferably aliphatic ketones, such as acetone, butanone, diisopropyl ketones; ethers, such as diethyl ether, diisopropyl ether, 1,2-dimethoxyethane, THF or dioxane; hydrocarbons, such as petroleum ether, cyclohexane, benzene or toluene; halogenated hydrocarbons, preferably chlorinated hydrocarbons, such as methylene chloride, chloroform, carbon tetrachloride, 1,2-dichloroethane, 1,1,2-trichloroethane or chlorobenzene; heterocyclics, such as pyrrolidine, piperidine or pyridine and mixtures of these solvents. These same solvents are also suitable for preparation of the mixed anhydrides of a compound of formula VIII. The reaction mixture is prepared and treated in conventional fashion.

In the compounds of Formula III, the radicals R$^2$ and R$^3$ are as defined above, especially those given as preferred. These compounds are 2-hydroxymercaptans or their alkali metal, alkaline earth metal or ammonium salts. Most of the mercaptans of the formula III are known, for example from published German patent application No. 22 56 537 and from published German patent application No. 23 59 955. New compounds of the formula III can be prepared in analogous fashion to that used for the known compound 2-hydroxy-2-methyl-heptanethiol, according to standard methods known from the literature, e.g., described in Example A of published German patent application No. 23 59 955.

The reaction of a compound of formula II with a thiol of formula III is conducted generally in the presence of a basic catalyst, an inert solvent being optional. Temperatures between about −20° and +50° C., preferably between 0° and 30° C. are typical. As solvents, there are preferred suitable alcohols, such as methanol or ethanol; hydrocarbons, such as benzene or toluene; or also water. Suitable basic catalysts include, e.g., alkali metal or alkaline earth metal hydroxides, such as NaOH, KOH or Ca(OH)$_2$; alkali metal alcoholates, such as NaOCH$_3$, NaOC$_2$H$_5$ or KO tert-C$_4$H$_9$; basic salts, preferably carbonates or acetates, such as K$_2$CO$_3$ or NaOCOCH$_3$; ammonia; amines, preferably secondary or tertiary amines, such as triethylamine, diisopropylamine, dicyclohexylamine, dimethylaniline, piperidine, 2,6-dimethylpiperidine, 2,2,6,6-tetramethylpiperidine, pyrrolidine, pyridine, quinoline, diaza-bicyclo[2.2.2]octane or diaza-bicyclo[3.4.0]nonene; but also primary amines, such as tert-butylamine or cyclohexylamine; or quaternary ammonium hydroxides, such as tetramethylammonium hydroxide or benzyltrimethylammonium hydroxide. It is especially advantageous to use one of these amines, especially a secondary or tertiary amine, simultaneously as the solvent and thus to work in the absence of an inert solvent.

The compounds of formula IV are obtainable from the compounds of formula IX

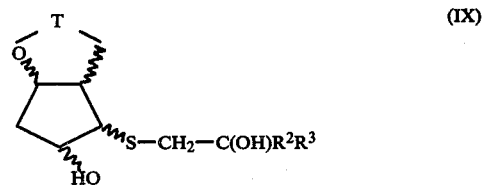

(IX)

wherein T is —CO— or —CHOR$^7$— and R$^7$ is methyl or ethyl; and R$^2$ and R$^3$ are as defined above; by reduction (when T is —CO—) with diisobutyl aluminum hydride in toluene at from about −90° to about −70° C., or by acid hydrolysis (when T is —CHOH—), e.g., with 0.03 N hydrochloric acid in acetonitrile/water mixtures at room temperature.

The compounds of the formula IX are in turn, preparable, e.g., by reaction of the known compounds Xa or Xb

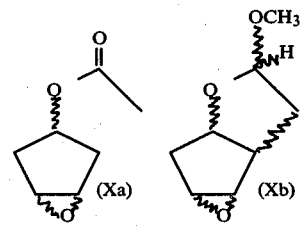

with a compound of the formula III.

Of the starting products of the formula Xa or Xb, those are, in particular, of importance in which all indicated bonds connect to the five-membered ring are in the α-configuration:

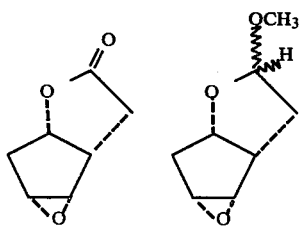

The compounds of formula IV are reacted with the compounds of formula V. In the compounds of the formula V, the residues Q and $R^4$ are as defined previously, especially those stated to be preferred. $R^6$ is an alkyl radical with 1–4 carbon atoms, preferably an unbranched alkyl radical, such as methyl, ethyl, propyl or butyl, but also a branched alkyl radical with 1–4 carbon atoms, such as isopropyl, sec-butyl, isobutyl or tert-butyl; in particular, however, $R^6$ is a phenyl group. Generally, all three radicals $R^6$ are the same but they can also be different. When $R^6$ is a branched alkyl radical, not more than two branched alkyl radicals, more preferably only one branched alkyl radical, is to be connected to the P-atom. X is Cl, Br or I, Br being preferred.

The compounds of formula V are new. They are prepared by analogous techniques to those used for the known phosphonium salts, such as 5-triphenylphosphoniopentanoic acid, according to methods known from the literature, for example, as described in published German patent application No. 24 31 930. One thereby reacts a phosphine $(R^6)_3P$, preferably triphenyl phosphine, with a compound of the formula XI

wherein X, Q and $R^4$ are defined above, especially those stated to be preferred.

The compounds of the formula XI are, in turn, new. They can be prepared in a simple manner according to standard methods known from the literature, e.g., by reaction of 5-chloro-, 5-bromo- or 5-iodopentanoic acid with a phenol of formula VII, for example in the presence of dicyclohexyl carbodiimide. Suitable reaction conditions include those mentioned above for the reaction of a compound of formula VII with a compound of formula VIII.

The reaction of a compound of the formula XI with a phosphine $(R^6)_3P$ is expediently carried out in an inert organic solvent. Hydrocarbons, such as cyclohexane, toluene, xylene and especially benzene are preferred, as well as acetonitrile. However, e.g., ethers, such as diethyl ether, diisopropyl ether, 1,2-dimethoxyethane or THF are also suitable reaction media. Suitable reaction temperatures lie between about 40° and 150° C., the boiling temperature of the reaction mixture being preferred.

The reaction of a compound of formula IV with a compound of formula V takes place analogously to the preparation of known compounds, such as $PGF_{2\alpha}$ or 2,3-trans-methano-11,15-bis-tetrahydropyranylprostaglandin $F_{2\alpha}$ according to standard methods known from the literature, e.g., described in published German patent application No. 24 31 930, for example, by the Wittig reaction (which employs a strong base, for example, of an alkali metal hydride, such as NaH; or a lithium alkyl compound, such as butyl lithium), preferably in dimethyl sulphoxide (DMSO) as solvent at temperatures between about 15° and about 80° C. It is especially expedient to work under an inert gas atmosphere, for example, nitrogen. In the compounds of formula I thereby obtained, B signifies a cis-C=C double bond.

In the compounds of formula VI, the residues A, B, $R^1$, $R^2$ and $R^3$ are as previously defined, especially those stated to be preferred. Most of the compounds of formula VI are known, for example from published German patent application No. 23 59 955 and published German patent application No. 24 22 924. New compounds of formula VI can be prepared by analogy to processes used to prepare the known 11,15-dihydroxy-9-oxo-13-thiaprostanoic acid according to standard methods known from the literature, for example, by the reaction of the corresponding compounds of formula III with 7-(2-oxo-1-cyclopenten-1-yl)-heptanoic acid, 7-(3-hydroxy-5-oxo-1-cyclopenten-1-yl)-heptanoic acid, 7-(2-oxo-1-cyclopenten-1-yl)-hept-5-enoic acid or 7-(2-hydroxy-5-oxo-1-cyclopenten-1-yl)-hept-5-enoic acid. From the so obtained compounds of formula VI (A=—CO—), can be prepared the compounds of formula VI (A=—CHOH—) by processes analogous to those used to prepare the known compound 9,11,15-trihydroxy-15-methyl-13-thia-prostanoic acid by reduction of the carbonyl group with standard methods known from the literature, for example with a complex metal hydride, such as $NaBH_4$. Suitable reactive acid derivatives of the compounds of formula VI, include all those which have been mentioned above as suitable with respect to the compounds of formula VIII.

In the compounds of the formula VII, Q and $R^4$ are as defined above, especially those mentioned as being preferred. Therefore, these are generally derivatives of p-aminophenol. Most of the compounds of formula VII are also known, for example from published German patent application No. 24 53 271. New compounds of the formula VII can be prepared by processes known from the literature, e.g. by acylation of p-aminophenol or 4-amino-1-naphthol with a compound, $R^4COOH$, or one of its reactive acid derivatives.

The reaction of a compound of formula VI or of one of its activated acid derivatives with a compound of formula VII can be carried out according to well known conventional methods. Preferably, the reaction conditions described above for the corresponding reactions of the compounds of formula VIII or their reactive acid derivatives with a compound of formula VII, are used.

Regarding the fourth mentioned preparative technique, the compounds which otherwise correspond to the formula I but in which at least one hydroxyl group and/or one carbonyl group is present in functionally changed form, can be prepared preferably according to processes by which the compounds of formula I are also obtainable. However, in the starting materials the corresponding hydroxyl groups and/or carbonyl group are present in appropriate functionally changed form. The residues by which these groups are functionally changed are those which are easily split off.

Suitable functionally changed OH groups include OH groups esterified with a saturated or unsaturated aliphatic, cycloaliphatic or aromatic substituted or unsubstituted carboxylic acid or sulphonic acid, or also an inorganic acid. Preferred carboxylic acid esters are derived from fatty acids which possess 1 to 18, preferably 1 to 6 carbon atoms, such as formic, acetic, butyric or isobutyric acid, but also include, e.g., pivalic, trichloroacetic, benzoic, p-nitrobenzoic, palmitic, stearic or oleic acid. Preferred sulphonic acid esters are derived from alkyl-sulphonic acids with 1 to 6 carbon atoms, e.g., methane- or ethane-sulphonic acid, or aryl-sulphonic acids with 6 to 10 carbon atoms, e.g., benzene-, p-toluene-, 1- and 2-naphthalene-sulphonic acid, and also from substituted sulphonic acids, such as 2-hydroxyethane- or 4-bromobenzene-sulphonic acid. Preferred inorganic acid esters are solphates and phosphates.

Suitable functionally changed OH groups can also be present in etherified form, e.g., as aralkoxy with preferably 7 to 19 carbon atoms, such as benzyloxy, p-methylbenzyloxy, 1- and 2-phenylethoxy, diphenylmethoxy, triphenylmethoxy, or 1- or 2-naphthylmethoxy; alkoxy with preferably up to 6 carbon atoms, such as methoxy, ethoxy or especially tert-butoxy; tetrahydropyranyloxy; or trialkylsilyloxy, preferably trimethylsilyloxy.

Keto groups can preferably be functionally changed as hemiketals, such as —$C(OH)(OR^8)$—, ketals, such as —$C(OR^8)_2$ or cyclic, e.g., ethylene, ketals, whereby the radicals $R^8$ can be the same or different and, generally signify lower alkyl radicals with 1 to 6 carbon atoms. Since the radicals $R^8$, however, only represent protective groups which are not present in the end products of the invention, their nature is non-critical.

Compounds which otherwise correspond to formula I but in which at least one hydroxyl group and/or carbonyl group is present in functionally changed form can be converted, according to methods known from the literature, with solvolysing agents into the compounds of formula I.

Solvolysing agents are preferably hydrolysing agents, such as water or water in admixture with organic solvents, usually in the presence of an acidic or basic catalyst. Suitable organic solvents include alcohols, such as methanol, ethanol, propanol, isopropanol, butanol, tert-butyl alcohol, amyl alcohol, 2-methoxyethanol or 2-ethoxyethanol; ethers, such as diethyl ether, THF, dioxane or 1,2-dimethoxyethane; acids, such as formic acid, acetic acid, propionic acid or butyric acid; esters, such as ethyl acetate or butyl acetate; ketones, such as acetone; amides, such as dimethyl formamide (DMF) or hexamethylphosphoric acid triamide (HMPT); nitriles, such as acetonitrile, sulphoxides, such as dimethyl sulphoxide (DMSO); and sulphones, such as tetrahydrothiophene-S,S-dioxide; as well as mixtures of these solvents.

Suitable acid catalysts for the solvolysis include inorganic acids, for example, hydrochloric sulphuric, phosphoric or hydrobromic acid; and organic acids, such as chloroacetic acid, trichloroacetic acid or trifluoroacetic acid, and methane-, ethane-, benzene or p-toluene-sulphonic acid. Suitable basic catalysts for the solvolysis include alkali metal or alkaline earth metal hydroxides, such as sodium, potassium or calcium hydroxide, or basic salts, such as sodium or potassium carbonate. Also included are organic bases, such as, for example, ethyl-, diethyl-, triethyl-, isopropyl-, n-butyl- or tri-n-butylamine, ethanolamine, triethanolamine, cyclohexylamine, dimethylaniline, pyrrolidine, piperidine, morpholine, pyridine, α-picoline or quinoline; or quaternary ammonium hydroxides, such as, e.g., tetramethylammonium hydroxide or benzyltrimethylammonium hydroxide. An excess of the catalyst can also be used in place of a solvent.

Suitable solvolysis time periods lie between about one hour and about 48 hours and suitable temperatures are between about −5° and about 80° C., preferably room temperature.

Regarding the fifth mentioned process, a compound of formula I (A=—CO—) can be reduced to the corresponding alcohol, e.g., with metal hydrides, especially complex metal hydrides. The reduction potential of the hydrides should be sufficiently low that the COO—Q group is not changed. Suitable reducing agents include sodium borohydride, possibly in the presence of lithium bromide; lithium borohydride; especially also complex trialkyl borohydrides, such as lithium hexyllimonyl borane, or borohydrides, such as lithium perhydro-9b-boroaphenalyl hydride; calcium borohydride; magnesium borohydride; lithium and sodium alkoxy aluminium hydrides, e.g., LiAl(O-tert-$C_4H_9$)$_3$H; and sodium trialkoxyborohydrides, e.g., sodium trimethoxyborohydride.

The reduction is expediently carried out in an inert solvent, for example an alcohol, especially an alkanol, such as methanol, ethanol or isopropyl alcohol; an ether, such as diethyl ether; THF or dioxane; or also in water, or in mixtures of these solvents at temperatures between −20° and 40° C., preferably at room temperature. The reaction times usually lie between 15 minutes and 6 hours.

The compounds of the formula I are generally obtained as mixtures of various stereoisomeric forms, i.e., as a rule, as mixtures of racemates. Racemates can be isolated from the racemate mixtures and obtained in pure form, for example, by recrystallization of the compounds themselves or of good crystallizing derivatives; but especially by chromatographic methods, including not only adsorption-chromatographic or partition-chromatographic methods but also mixed forms. The racemates can be separated into their optical antipodes according to well known conventional methods, such as are described in the literature. The method of chemical separation is preferred.

Thus, for example, by esterifying OH groups with optically-active acids, such as (+)- or (−)-tartaric acid or camphoric acid, or by reacting keto groups with optically-active hydrazines, such as methyl hydrazine, pure enantiomers can be obtained from these derivatives. Furthermore, it is, of course, also possible to obtain optically-active compounds using the above-described preparative methods by using starting materials which are themselves optically-active.

It has been found that the 13-thiaprostanoic acid derivatives of Formula I possess valuable pharmacological properties in mammals, including humans. For example, and particularly in the case of the compounds with A=—CO—, blood pressure-lowering activity has been observed as evidenced by the result of tests on spontaneously hypertensive rats. In this test, the test substances are given by gavage, and the decrease in blood pressure is measured by tail plethysmography. The blood pressure-lowering activity can also be observed in tests on barbiturate-narcotised cats using continuous infusion. Here the arterial blood pressure is recorded kymographically; the test substances are diffused in over a period of time of 10 minutes in aqueous propylene glycol solution.

In contrast to the acid form of these prostaglandins, the esters of this invention have an outstandingly high gastric tolerance in oral administration. This surprisingly low incidence of undesirable side effects can be demonstrated in the following test: the test substances are given orally in gelatin capsules to fasted mongrel dogs and their vomiting threshold is assessed. The gastric tolerance of these substances can also be proved by observation of their diarrhea-inducing activity on spontaneously hypertensive rats. This test can be conducted simultaneously with the evaluation of the blood pressure-lowering effect of these substances. Still another method for demonstrating the degree of the gastric tolerance of these esters is the evaluation of the respiratory tract response in anaesthetized dogs after administration of the test substances. In this test, the trial compounds are given intravenously to artificially ventilated anaesthetized dogs and the change of the intratracheal pressure is measured by a pressure transducer.

Furthermore, for the 13-thiaprostanoic acid derivatives of formula I, there can be ascertained other pharmaceutical activities such as vasodilatory, antiphlogistic, diuretic and bronchial-relaxing activities, as well as activities for inhibiting gastric juice secretion, thrombocyte aggregation, lipid breakdown and noradrenaline-liberation. Moreover, nasal mucosa decongesting properties can be observed. All these effects can be determined by the methods conventional for these purposes. The compounds of formula I can also influence the function of the corpus luteum, the ova transport through the Fallopian tubes, nidation and fertility. Thus, especially the compounds of formula I with B=cis-1,2-vinylene, exhibit an oestrus-synchronizing action, for example in cattle.

Pharmaceutically effective amounts of the new compounds of formula I can be mixed with at least one solid, liquid and/or semi-liquid carrier or adjuvant material conventional in pharmacy. Such compositions can be used as pharmaceuticals in human or veterinary medicine. Suitable carrier materials include organic or inorganic materials which are suitable for parenteral, enteral (e.g. oral) or topical administration, for example, water, vegetable oils, benzyl alcohol, polyethylene glycols, glycerol triacetate, gelatine, lactose, starch, magnesium stearate, talc, vaseline, cholesterol, etc. For oral administration, tablets, dragees, capsules, syrups, juices or drops, are suitable; for rectal administration, suppositories are typical; for parenteral administration, solutions, preferably oily or aqueous solutions, and also suspensions, emulsions or implants are included; and for topical application, salves, creams or powders are customary.

The new compounds can also be lyophilized. The resultant lyophilizates can be used, e.g., for the preparation of injection preparations. The aforementioned compositions can also be sterilized or mixed with adjuvant materials, such as lubricating, preserving, stabilizing or wetting agents, emulsifiers, salts for the influencing of the osmotic pressure, buffer substances, coloring, flavoring and/or aroma-generating materials, etc. If desired, they can also contain one or more additional active materials, e.g., one or more vitamins, etc.

The compounds of formula I are preferably administered in a dosage of from 0.01 to 200 mg. per dosage unit. The dosing is dependent upon the treated species, the form of administration and the purpose of the treatment. Suitable dosages can also be below or above these values, in accordance with conventional considerations.

If, for example, one wishes to utilize the oestrus-synchronizing action of the compounds of formula I, especially of the formulae Ic, If, Ig, Ij and Ik, it is especially advantageous to inject intramuscularly, e.g., cattle (cows or heifers), with about 0.1 mg. up to about 30 mg., preferably about 0.5 mg. up to about 20 mg., especially about 1.5 mg. up to about 15 mg., of the active material. It is favorable to administer the effective dose by single injection between about the 7th day and about the 12th day of the cycle but one can also inject several partial doses optionally distributed over several days, or the effective dose on two different days, e.g., on the 1st and on the 3rd day. Also, in other domestic animals, for example, dogs, horses, sheep and pigs, the oestrus can be synchronized by administration of a compound of the formula I, especially of the formulae Ie, If, Ig, Ij and Ik. The effective dose varies in dependence upon the average body weight of the treated species and can, without difficulty, be determined by the skilled artisan by conventional considerations, e.g., by reference to the given recommended values for cattle.

Since the compounds of formula I crystalize well, they can also be advantageously employed for the purification of 13-thiaprostaglandins with a free carboxyl group, for example, of the 13-thiaprostaglandins of the formula VI which, in general, are obtained as oils which are difficult to purify. After conversion of these oils into the well crystallizing compounds of formula I, if necessary, the latter can be simply recrystallized from conventional solvents using well known conventional techniques. The pure compounds of formula I can then be hydrolyzed also using well known conventional techniques, e.g., enzymatically in analogy with the method described in published German Patent Application No. 22 42 792.

On the basis of these crystalline properties, the compounds of formula I can also be handled especially simply in the preparation of pharmaceutical compositions, for example of tablets. Furthermore, the esters according to this invention are surprisingly stable compounds with excellent storage stability. In comparison with the free acids, they suffer less from acid-catalyzed or base-catalyzed decomposition and have, therefore, better stability, especially also in solution.

Without further elaboration, it is believed that one skilled in the art can, using the preceding description, utilize the present invention to its fullest extent.

The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

IR spectra (IR) are characterized by description of the principal bands (as film). The NMR spectra were measured in $CDCl_3$ against tetramethylsilane and characterized by description of the signals in ppm. The following symbols are used: m=multiplet; q=quartet; t=triplet; d=doublet and s=single band. Each of the compounds of formula I mentioned in the following Examples is especially suitable for the preparation of pharmaceuticals.

EXAMPLE 1

0.326 g. of 7-(3-Hydroxy-5-oxo-1-cyclopenten-1-yl)-heptanoic acid were dissolved in 20 ml. of dry acetone. At −20° C., 0.23 ml. of triehtylamine were added and then 0.216 ml. isobutyl chloroformate. After 5 minutes, the temperature was permitted to increase to 25° C., and 0.4 g. of p-benzoylaminophenol dissolved in 10 ml. of dry pyridine was added dropwise. After 2 hours, the solvent was distilled off; the residue was extracted in ethyl acetate; the organic phase was washed with water and dried over sodium sulphate. The solvent was distilled off. After chromatographic purification of the residue (silica gel/ethyl acetate), 7-(3-hydroxy-5-oxo-1-cyclopenten-1-yl)-heptanoic acid p-benzoylaminophenyl ester (m.p. 168°–169° C.) was obtained.

Analogously, from 7-(3-hydroxy-5-oxo-1-cyclopenten-1-yl)-heptanoic acid, after reaction with isobutyl chloroformate and reaction of the mixed anhydride obtained with the corresponding phenol of formula VII, the following esters (formula II; $R^1$=OH, A=—CO—, B=—CH$_2$CH$_2$—) can be prepared:

7-(3-hydroxy-5-oxo-1-cyclopenten-1-yl)-heptanoic acid p-acetylaminophenyl ester,
7-(3-hydroxy-5-oxo-1-cyclopenten-1-yl)-heptanoic acid p-(p-benzoylaminobenzoylamino)-phenyl ester,
7-(3-hydroxy-5-oxo-1-cyclopenten-1-yl)-heptanoic acid p-ureidophenyl ester,
7-(3-hydroxy-5-oxo-1-cyclopenten-1-yl)-heptanoic acid (3-phenylureido)-phenyl ester,
7-(3-hydroxy-5-oxo-1-cyclopenten-1-yl)-heptanoic acid (4-acetylaminol-1-naphthyl)-ester,
7-(3-hydroxy-5-oxo-1-cyclopenten-1-yl)-heptanoic acid p-acetylaminobenzoylamino)-phenyl ester,
7-(3-hydroxy-5-oxo-1-cyclopenten-1-yl)-heptanoic acid (4-benzoylamino-1-naphthyl) ester and
7-(3-hydroxy-5-oxo-1-cyclopenten-1-yl)-heptanoic acid (4-ureido-1-naphthyl) ester.

EXAMPLE 2

Analogously to Example 1, from 7-(5-oxo-1-cyclopenten-1-yl)-heptanoic acid, after reaction with isobutyl formate and reaction of the mixed anhydride obtained with the corresponding phenol of the formula VII, the following esters (formula II; $R^1$=H, A=—CO=, B=—CH$_2$CH$_2$—) can be prepared:

7-(5-oxo-1-cyclopenten-1-yl)-heptanoic acid p-benzoylaminophenyl ester,
7-(5-oxo-1-cyclopenten-1-yl)-heptanoic acid p-acetylamino phenyl ester.
7-(5-oxo-1-cyclopenten-1-yl)-heptanoic acid 1-(p-acetylaminobenzoylamino)-phenyl ester,
7-(5-oxo-1-cyclopenten-1-yl)-heptanoic acid p-(p-benzoylaminobenzoylamino)-phenyl ester,
7-(5-oxo-1-cyclopenten-1-yl)-heptanoic acid p-ureidophenyl ester,
7-(5-oxo-1-cyclopenten-1-yl)-heptanoic acid p-(3-phenylureido)-phenyl ester,
7-(5-oxo-1-cyclopenten-1-yl)-heptanoic acid (4-acetylamino-1-naphthyl) ester,
7-(5-oxo-1-cyclopenten-1-yl)-heptanoic acid (4-benzoylamino-1-naphthyl) ester and
7-(5-oxo-1-cyclopenten-1-yl)-heptanoic acid (4-ureido-1-naphthyl) ester.

EXAMPLE 3

Analogously to Example 1, from 7-(5-oxo-1-cyclopenten-1-yl)-hept-5-cis-enoic acid, after reaction with isobutyl formate and reaction of the mixed anhydride obtained with the corresponding phenol of the formula VII, the following esters (formula II, $R^1$=H, A=—CO—, B=cis—CH=CH—) can be prepared:

7-(5-oxo-1-cyclopenten-1-yl)-hept-5-cis-enoic acid p-benzoylaminophenyl ester,
7-(5-oxo-1-cyclopenten-1-yl)-hept-5-cis-enoic acid p-acetylaminophenyl ester,
7-(5-oxo-1-cyclopenten-1-yl)-hept-5-cis-enoic acid p-(p-acetylaminobenzoylamino)-phenyl ester,
7-(5-oxo-1-cyclopenten-1-yl)-hept-5-cis-enoic acid p-(p-benzoylaminobenzoylamino)-phenyl ester,
7-(5-oxo-1-cyclopenten-1-yl)-hept-5-cis-enoic acid p-ureidophenyl ester,
7-(5-oxo-1-cyclopenten-1-yl)-hept-5-cis-enoic acid p-(3-phenylureido)-phenyl ester,
7-(5-oxo-1-cyclopenten-1-yl)-hept-5-cis-enoic acid (4-acetylamino-1-naphthyl) ester,
7-(5-oxo-1-cyclopenten-1-yl)-hept-5-cis-enoic acid (4-benzoylamino-1-naphthyl) ester and
7-(5-oxo-1-cyclopenten-1-yl)-hept-5-cis-enoic acid (4-ureido-1-naphthyl) ester.

EXAMPLE 4

Analogously to Example 1, from 7-(3-hydroxy-5-oxo-1-cyclopenten-1-yl)-hept-5-cis-enoic acid, after reaction with isobutyl formate and reaction of the mixed anhydride obtained with the corresponding phenol of the formula VII, the following esters (formula II; $R^1$=OH, A=—CO—, B=cis—CH=CH—) can be prepared:

7-(3-hydroxy-5-oxo-1-cyclopenten-1-yl)-hept-5-cis-enoic acid p-benzoylaminophenyl ester,
7-(3-hydroxy-5-oxo-1-cyclopenten-1-yl)-hept-5-cis-enoic acid p-acetylaminophenyl ester,
7-(3-hydroxy-5-oxo-1-cyclopenten-1-yl)-hept-5-cis-enoic acid p-(p-acetylaminobenzoylamino)-phenyl ester,
7-(3-hydroxy-5-oxo-1-cyclopenten-1-yl)-hept-5-cis-enoic acid p-(p-benzoylaminobenzoylamino)-phenyl ester,
7-(3-hydroxy-5-oxo-1-cyclopenten-1-yl)-hept-5-cis-enoic acid p-ureidophenyl ester,
7-(3-hydroxy-5-oxo-1-cyclopenten-1-yl)-hept-5-cis-enoic acid p-(3-phenylureido)-phenyl ester,
7-(3-hydroxy-5-oxo-1-cyclopenten-1-yl)-hept-5-cis-enoic acid (4-acetylamino-1-naphthyl) ester,
7-(3-hydroxy-5-oxo-1-cyclopenten-1-yl)-hept-5-cis-enoic acid (4-benzoylamino-1-naphthyl) ester and
7-(3-hydroxy-5-oxo-1-cyclopenten-1-yl)-hept-5-cis-enoic acid (4-ureido-1-naphthyl) ester.

EXAMPLES 5–23

1.4 g. of 7-(3-Hydroxy-5-oxo-1-cyclopenten-1-yl)-heptanoic acid p-benzoylaminophenyl ester were dissolved in 40 ml. of methanol, 2.8 ml. of 2-hydroxy-2-methyl-heptanethiol were added thereto. The mixture was cooled under an atmosphere of nitrogen to 7° C. 2.24 ml. of diisopropylamine dissolved in 5 ml. of methanol were added dropwise thereto. The mixture was stirred for 30 minutes at 7° C. 15 ml. of Chloroform was added thereto, stirring was carried out for a further 15 minutes. The solution was poured into 100 ml. of ice water and the pH value adjusted with citric acid to 3–4. The product was extracted with chloroform; the organic phase washed with water and dried over sodium sulphate. The solvent was distilled off. After chromatographic purification of the residue (silica gel/ethyl acetate), 11α,15-dihydroxy-15-methyl-9-oxo-13-thiaprostanoic acid p-benzoylaminophenyl ester, m.p. 74°–76° C. (from diethyl ether), was obtained.

Analogously to Example 5, by reaction of 7-(3-hydroxy-5-oxo-1-cyclopenten-1-yl)-heptanoic acid p-benzoylaminophenyl ester with the corresponding thiols of formula III, mentioned in Example 95b the compounds of formula I mentioned in the following Examples 6a to 23 are preparable:

| Example | Compound of the formula I |
|---|---|
| 6a | 11α,15α-dihydroxy-9-oxo-13-thiaprostanoic acid p-benzoylaminophenyl ester, NMR: 0,77 ppm, 1,3 ppm, 2,0–3,0 ppm (m), 4,2 ppm, 6,9–7,9 ppm, (m), |
| 6b | 11α,15β-dihydroxy-9-oxo-13-thiaprostanoic acid p-benzoylaminophenyl ester, NMR: 0,88 ppm, 1,2–1,6 ppm (m), 2,0–3,0 ppm (m) 3,85 ppm (t), 4,3 ppm, 7,0–8,0 ppm (m), |
| 7 | 11α,15-dihydroxy-16-methyl-9-oxo-13-thiaprostanoic acid p-benzoylaminophenyl ester, m.p. = 72–74°, |
| 8 | 11α,15-dihydroxy-15,16-dimethyl-9-oxo-13-thiaprostanoic acid p-benzoylaminophenyl ester, m.p. = 82–83°, |
| 9 | 11α,15-dihydroxy-16,16-dimethyl-9-oxo-13-thiaprostanoic acid p-benzoylaminophenyl ester, |
| 10 | 11α,15-dihydroxy-9-oxo-17-phenyl-13-thia-18,19,20-trinorprostanoic acid p-benzoylaminophenyl ester, |
| 11 | 11α,15-dihydroxy-15-methyl-9-oxo-17-phenyl-13-thia-18,19,20-trinorprostanoic acid p-benzoylaminophenyl ester, |
| 12 | 11α,15-dihydroxy-9-oxo-17-m-trifluoromethylphenyl-13-thia-18,19,20-trinorprostanoic acid p-benzoylaminophenyl ester, |
| 13 | 11α,15-dihydroxy-15-methyl-9-oxo-17-m-trifluoromethylphenyl-13-thia-18,19,20-trinorprostanoic acid p-benzoylaminophenyl ester, |
| 14 | 11α,15-dihydroxy-9-oxo-17-m-chlorophenyl-13-thia-18,19,20-trinorprostanoic acid p-benzoylaminophenyl ester, |
| 15 | 11α,15-dihydroxy-15-methyl-9-oxo-17-m-chlorophenyl-13-thia-18,19,20-trinorprostanoic acid p-benzoylaminophenyl ester, |
| 16 | 11α,15-dihydroxy-9-oxo-16-phenoxy-13-thia-17,18,19,20-tetranorprostanoic acid p-benzoylaminophenyl ester, |
| 17 | 11α,15-dihydroxy-15-methyl-9-oxo-16-phenoxy-13-thia-17,18,19,20-tetranorprostanoic acid p-benzoylaminophenyl ester, |
| 18 | 11α,15-dihydroxy-9-oxo-16-m-chlorophenoxy-13-thia-17,18,19,20-tetranorprostanoic acid p-benzoylaminophenyl ester, |
| 19 | 11α,15-dihydroxy-15-methyl-9-oxo-16-m-chlorophenoxy-13-thia-17,18,19,20-tetranorprostanoic acid p-benzoylaminophenyl ester, |
| 20 | 11α,15-dihydroxy-9-oxo-16-m-trifluoromethylphenoxy-13-thia-17,18,19,20-tetranorprostanoic acid p-benzoylaminophenyl ester, |
| 21 | 11α,15-dihydroxy-15-methyl-9-oxo-16-m-trifluoromethylphenoxy-13-thia-17,18,19,20-tetranorprostanoic acid p-benzoylaminophenyl ester, |
| 22 | 11α,15-dihydroxy-9-oxo-16-m-methoxyphenoxy-13-thia-17,18,19,20-tetranorprostanoic acid p-benzoylaminophenyl ester, |
| 23 | 11α,15-dihydroxy-15-methyl-9-oxo-16-m-methoxyphenoxy-13-thia-17,18,19,20-tetranorprostanoic acid p-benzoylaminophenyl ester. |

EXAMPLES 24–42

Analogously to Example 5, by reaction of 7-(3-hydroxy-5-oxo-1-cyclopenten-1-yl)-hept-5-enoic acid p-benzoylaminophenyl ester with 2-hydroxy-2-methylheptanethiol in the presence of diisopropylamine, 11α,15-dihydroxy-15-methyl-9-oxo-13-thia-5-prostenoic acid p-benzoylaminophenyl ester is obtained.

Analogously to Example 24, by the reaction of 7-(3-hydroxy-5-oxo-1-cyclopenten-1-yl)-hept-5-enoic acid p-benzoylaminophenyl ester with the corresponding thiol of formula III mentioned in Example 95b, the compounds of formula I mentioned in the following Examples 25 to 42 are obtainable:

| Example | Compound of the formula I |
|---|---|
| 25 | 11α,15-dihydroxy-9-oxo-13-thia-5-prostenoic acid p-benzoylaminophenyl ester, |
| 26 | 11α,15-dihydroxy-16-methyl-9-oxo-13-thia-5-prostenoic acid p-benzoylaminophenyl ester, |
| 27 | 11α,15-dihydroxy-15,16-dimethyl-9-oxo-13-thia-5-prostenoic acid p-benzoylaminophenyl ester, |
| 28 | 11α,15-dihydroxy-16,16-dimethyl-9-oxo-13-thia-5-prostenoic acid p-benzoylaminophenyl ester, |
| 29 | 11α,15-dihydroxy-9-oxo-17-phenyl-13-thia-18,19,20-trinor-5-prostenoic acid p-benzoylaminophenyl ester, |
| 30 | 11α,15-dihydroxy-15-methyl-9-oxo-17-phenyl-13-thia-18,19,20-trinor-5-prostenoic acid p-benzoylaminophenyl ester |
| 31 | 11α,15-dihydroxy-9-oxo-17-m-trifluoromethylphenyl-13-thia-18,19,20-trinor-5-prostenoic acid p-benzoylaminophenyl ester |
| 32 | 11α,15-dihydroxy-15-methyl-9-oxo-17-m-trifluoromethylphenyl-13-thia-18,19,20-trinor-5-prostenoic acid p-benzoylaminophenyl ester |
| 33 | 11α,15-dihydroxy-9-oxo-17-m-chlorophenyl-13-thia-18,19,20-trinor-5-prostenoic acid p-benzoylaminophenyl ester |
| 34 | 11α,15-dihydroxy-15-methyl-9-oxo-17-m-chlorophenyl-13-thia-18,19,20-trinor-5-prostenoic acid l-benzoylaminophenyl ester |
| 35 | 11α,15-dihydroxy-9-oxo-16-phenoxy-13-thia-17,18,19,20-tetranor-5-prostenoic acid p-benzoylaminophenyl ester |
| 36 | 11α,15-dihydroxy-15-methyl-9-oxo-16-phenoxy-13-thia-17,18,19,20-tetranor-5-prostenoic acid p-benzoylaminophenyl ester |
| 37 | 11α,15-dihydroxy-9-oxo-16-m-chlorophenoxy-13-thia-17,18,19,20-tetranor-5-prostenoic acid p-benzoylaminophenyl ester |
| 38 | 11α,15-dihydroxy-15-methyl-9-oxo-16-m-chlorophenoxy-13-thia-17,18,19,20-tetranor-5-prostenoic acid p-benzoylaminophenyl ester |
| 39 | 11α,15-dihydroxy-9-oxo-16-m-trifluoromethylphenoxy-13-thia-17,18,19,20-tetranor-5-prostenoic acid p-benzoylaminophenyl ester |
| 40 | 11α,15-dihydroxy-15-methyl-9-oxo-16-m-trifluoromethylphenoxy-13-thia-17,18,19,20-tetranor-5-prostenoic acid p-benzoylaminophenyl ester |
| 41 | 11α,15-dihydroxy-9-oxo-16-m-methoxyphenoxy-13-thia-17,18,19,20-tetranor-5-prostenoic acid p-benzoylaminophenyl ester |
| 42 | 11α,15-dihydroxy-15-methyl-9-oxo-16-m-methoxyphenoxy-13-thia-17,18,19,20-tetranor-5-prostenoic acid p-benzoylaminophenyl ester |

EXAMPLES 43–80

Under nitrogen, 1.3 g. of 11α,15-dihydroxy-15-methyl-9-oxo-13-thiaprostanoic acid p-benzoylaminophenyl ester, dissolved in 40 ml. of dry THF was added to a suspension of 3.3 g. of LiAl(O-tert.—$C_4H_9$)$_3$H in 25 ml. of dry THF. The solution was allowed to stand for 1 hour at room temperature; then poured into 90 ml. of ice-cold 1 N HCl; and extracted with CHCl$_3$. The organic phase was washed with water and dried over NaSO$_4$. The solvent was distilled off. After chromatographic purification of the residue (silica gel/ethyl acetate), 9,11α,15-trihydroxy-15-methyl-13-thiaprostanoic acid p-benzoylaminophenyl ester was obtained.

Analogously to Example 43, by reduction of the keto compounds of formula I (A=—CO—) mentioned in Examples 6 to 42 with LiAl(O-tert.—$C_4H_9$)$_3$H, there are obtainable the compounds of the formula I (A=—CHOH—) mentioned in the following Examples 44 to 80:

| Example | Compound of the formula I |
|---|---|
| 44 | 9,11α,15-trihydroxy-13-thiaprostanoic acid p- |

| Example | Compound of the formula I |
|---|---|
| | benzoylaminophenyl ester |
| 45 | 9,11α,15-trihydroxy-16-methyl-13-thiaprostanoic acid p-benzoylaminophenyl ester |
| 46 | 9,11α,15-trihydroxy-15,16-dimethyl-13-thiaprostanoic acid p-benzoylaminophenyl ester |
| 47 | 9,11α,15-trihydroxy-16,16-dimethyl-13-thiaprostanoic acid p-benzoylaminophenyl ester |
| 48 | 9,11α,15-trihydroxy-17-phenyl-13-thia-18,19,20-trinorprostanoic acid p-benzoylaminophenyl ester |
| 49 | 9,11α,15-trihydroxy-15-methyl-17-phenyl-13-thia-18,19,20-trinorprostanoic acid p-benzoylaminophenyl ester |
| 50 | 9,11α,15-trihydroxy-17-m-trifluoromethylphenyl-13-thia-18,19,20-trinorprostanoic acid p-benzoylaminophenyl ester |
| 51 | 9,11α,15-trihydroxy-15-methyl-17-m-trifluoromethylphenyl-13-thia-18,19,20-trinorprostanoic acid p-benzoylaminophenyl ester |
| 52 | 9,11α,15-trihydroxy-17-m-chlorophenyl-13-thia-18,19,20-trinorprostanoic acid p-benzoylamino phenyl ester |
| 53 | 9,11α,15-trihydroxy-15-methyl-17-m-chlorophenyl-13-thia-18,19,20-trinorprostanoic acid p-benzoylaminophenyl ester |
| 54 | 9,11α,15-trihydroxy-16-phenoxy-13-thia-17,18,19,20-tetranorprostanoic acid p-benzoylaminophenyl ester |
| 55 | 9,11α,15-trihydroxy-15-methyl-16-phenoxy-13-thia-17,18,19,20-tetranorprostanoic acid p-benzoylaminophenyl ester |
| 56 | 9,11α,15-trihydroxy-16-m-chlorophenoxy-13-thia-17,18,19,20-tetranorprostanoic acid p-benzoylaminophenyl ester |
| 57 | 9,11α,15-trihydroxy-15-methyl-16-m-chlorophenoxy-13-thia-17,18,19,20-tetranorprostanoic acid p-benzoylaminophenyl ester |
| 58 | 9,11α,15-trihydroxy-16-m-trifluoromethylphenoxy-13-thia-17,18,19,20-tetranorprostanoic acid p-benzoylaminophenyl ester |
| 59 | 9,11α,15-trihydroxy-15-methyl-16-m-trifluoromethylphenoxy-13-thia-17,18,19,20-tetranorprostanoic acid p-benzoylaminophenyl ester |
| 60 | 9,11α,15-trihydroxy-16-m-methoxyphenoxy-13-thia-17,18,19,20-tetranorprostanoic acid p-benzoylaminophenyl ester |
| 61 | 9,11α,15-trihydroxy-15-methyl-16-m-methoxyphenoxy-13-thia-17,18,19,20-tetranorprostanoic acid p-benzoylaminophenol ester |
| 62 | 9,11α,15-trihydroxy-15-methyl-13-thia-5-prostenoic acid p-benzoylaminophenyl ester |
| 63 | 9,11α,15-trihydroxy-13-thia-5-prostenoic acid p-benzoylaminophenyl ester |
| 64 | 9,11α,15-trihydroxy-16-methyl-13-thia-5-prostenoic acid p-benzoylaminophenyl ester |
| 65 | 9,11α,15-trihydroxy-15,16-dimethyl-13-thia-5-prostenoic acid p-benzoylaminophenyl ester |
| 66 | 9,11α,15-trihydroxy-16,16-dimethyl-13-thia-5-prostenoic acid p-benzoylaminophenyl ester |
| 67 | 9,11α,15-trihydroxy-17-phenyl-13-thia-18,19,20-trinor-5-prostenoic acid p-benzoylaminophenyl ester |
| 68 | 9,11α,15-trihydroxy-15-methyl-17-phenyl-13-thia-18,19,20-trinor-5-prostenoic acid p-benzoylaminophenyl ester |
| 69 | 9,11α,15-trihydroxy-17-m-trifluoromethylphenyl-13-thia-18,19,20-trinor-5-prostenoic acid p-benzoylaminophenyl ester |
| 70 | 9,11α,15-trihydroxy-15-methyl-17-m-trifluoromethylphenyl-13-thia-18,19,20-trinor-5-prostenoic acid p-benzoylaminophenyl ester |
| 71 | 9,11α,15-trihydroxy-17-m-chlorophenyl-13-thia-18,19,20-trinor-5-prostenoic acid p-benzoylaminophenyl ester |
| 72 | 9,11α,15-trihydroxy-15-methyl-17-m-chlorophenyl-13-thia-18,19,20-trinor-5-prostenoic acid p-benzoylaminophenyl ester |
| 73 | 9,11α,15-trihydroxy-16-phenoxy-13-thia-18,19,20-trinor-5-prostenoic acid p-benzoylaminophenyl ester |
| 74 | 9,11α,15-trihydroxy-15-methyl-16-phenoxy-13-thia-17,18,19,20-tetranor-5-prostenoic acid p-benzoylaminophenyl ester |
| 75 | 9,11α,15-trihydroxy-16-m-chlorophenoxy-13-thia-17,18,19,20-tetranor-5-prostenoic acid p-benzoylaminophenyl ester |
| 76 | 9,11α,15-trihydroxy-15-methyl-16-m-chlorophenoxy-13-thia-17,18,19,20-tetranor-5-prostenoic acid p-benzoylaminophenyl ester |
| 77 | 9,11α,15-trihydroxy-16-m-trifluoromethylphenoxy-13-thia-17,18,19,20-tetranor-5-prostenoic acid p-benzoylaminophenyl ester |
| 78 | 9,11α,15-trihydroxy-15-methyl-16-m-trifluoromethylphenoxy-13-thia-17,18,19,20-tetranor-5-prostenoic acid p-benzoylaminophenyl ester |
| 79 | 9,11α,15-trihydroxy-16-m-methoxyphenoxy-13-thia-17,18,19,20-tetranor-5-prostenoic acid p-benzoylaminophenyl ester |
| 80 | 9,11α,15-trihydroxy-15-methyl-16-m-methoxyphenoxy-13-thia-17,18,19,20-tetranor-5-prostenoic acid p-benzoylaminophenyl ester |

EXAMPLE 81

A mixture of 5.02 g. of 7-(3-hydroxy-5-oxo-2-bromocyclopent-1-yl)-heptanoic acid p-benzoylaminophenyl ester (preparable from 7-(3-hydroxy-5-oxo-1-cyclopenten-1-yl)-heptanoic acid p-benzoylaminophenyl ester by the addition of HBr), 60 ml. of dry ethanol and 1.9 g. of sodium 2-hydroxy-2-methylheptane-thiolate was stirred for 3 hours at 0° C. The mixture was permitted to stand for 2 hours at room temperature. 30 ml. of a saturated aqueous NaCl solution was added thereto. The solution was extracted with chloroform. The organic phase was washed with water and dried over Na$_2$SO$_3$. The solvent was distilled off. After chromatographic purification of the residue (silica gel/ethyl acetate), 11,15-dihydroxy-15-methyl-9-oxo-13-thiaprostanoic acid p-benzoylaminophenyl ester, m.p. 74°–76° (from diethyl ether) was obtained.

EXAMPLE 82

A mixture of 5.01 g. of 7-(2-hydroxy-4,5-cis-epoxy-cyclopent-1-yl)-hept-5-enoic acid p-benzoylaminophenyl ester, 60 ml. of dry ethanol and 2 g. of sodium 2-hydroxy-2-methylheptane-thiolate was stirred for 4 hours at room temperature. 30 ml. of saturated aqueous NaCl solution was added thereto. The solution was extracted with chloroform. The organic phase was washed with water and dried over Na$_2$SO$_4$. The solvent was distilled off. After chromatographic purification of the residue (silica gel/ethyl acetate), 11,15-dihydroxy-15-methyl-9-oxo-13-thiaprostanoic acid p-benzoylaminophenyl ester, m.p. 74°–76° C. (from diethyl ether) was obtained.

The starting compound was obtained as follows. Under nitrogen, a solution of 5.6 g. of 5-triphenylphosphoniopentanoic acid p-benzoylaminophenyl ester bromide, dissolved in 15 ml. of dry DMSO was added dropwise to a stirred solution, which had been obtained by the addition of 1.25 g. of NaH (as a 50% suspension in mineral oil) to 100 ml. of dry DMSO. The mixture was maintained for 1 hour at 80° C. After cooling to room temperature, there was added dropwise, under nitrogen and with stirring, 1.4 g. of 2-oxa-3-hydroxy-6,7-cis-epoxy-cis-bicyclo[3.3.0]octane (obtainable from 2-oxa-6,7-cis-epoxy-3-oxo-cis-bicyclo[3.3.0]octane—described in J. Amer. Chem. Soc. 94, 4344 [1972]—by reduction with diisobutyl aluminum hydride in toluene at −78° C.) dissolved in 8 ml. of dry DMSO in order to dissolve the phosphorylide. The solution was stirred for a further 2 hours at 50° C. After cooling, the reaction mixture was poured into a mixture consisting of 10 ml. of ethyl acetate, 40 g. of dry ice and 50 ml. of water. The organic phase was separated. The aqueous phase was washed three times with 50 ml. amounts of ethyl acetate containing 20 g. of dry ice. The combined organic phases were washed with water and dried over $MgSO_4$. The solvent was distilled off. After chromatographic purification of the residue (silica gel/chloroform) 7-(2-hydroxy-4,5-cis-epoxy-cyclopent-1-yl)-hept-5-enoic acid p-benzoylaminophenyl ester was obtained.

EXAMPLE 83

Under nitrogen a solution of 5.6 g. of 5-triphenylphosphoniopentanoic acid p-benzoylaminophenyl ester bromide, dissolved in 15 ml. of dry DMSO was dropped into a stirred solution which had been obtained by the addition of 0.75 g. of NaH (as a 50% suspension in mineral oil) to 10 ml. of dry DMSO. The mixture was maintained for 1 hour at 80° C. After cooling to room temperature, there was added dropwise, under nitrogen and with stirring, 3 g. of 2-oxa-3,7-dihydroxy-6-(2-hydroxy-2-methyl-heptylmercapto)-bicyclo[3.3.0]octane, dissolved in 5 ml. of dry DMSO, to the solution of the phosphorylide. The solution was stirred for a further 2 hours at 50° C. After cooling, the reaction mixture was poured into a mixture consisting of 10 ml. of ethyl acetate, 40 g of dry ice and 50 ml of water. The organic phase was separated off. The aqueous phase was washed three times with 50 ml amounts of ethyl acetate containing 20 g. of dry ice. The combined organic phases were washed with water and dried over $MgSO_4$. The solvent was distilled off. After chromatographic purification of the residue (silica gel/chloroform), 9,11,15-trihydroxy-15-methyl-13-thia-5-prostenoic acid p-benzoylaminophenyl ester was obtained.

EXAMPLES 84–92

A mixture of 1.24 g. of 9α,11α,15-trihydroxy-16-m-chlorophenoxy-13-thia-17,18,19,20-tetranor-5-prostenoic acid, 0.46 ml. of triethylamine and 40 ml. of acetone was cooled to −20° C. 0.432 ml. of isobutyl chloroformate was added dropwise. After 5 minutes the solution was warmed to 25° C. 0.8 g. of p-benzoylaminophenol, dissolved in 20 ml. of dry pyridine, was added dropwise therein. The solution was stirred for 2 hours at room temperature. The solvent was distilled off and the residue extracted in ethyl acetate. The organic phase was washed with water and dried over $Na_2SO_4$. The solvent was distilled off. After chromatographic purification of the residue (silica gel/ethyl acetate), 9α,11α,15-trihydroxy-16-m-chlorophenoxy-13-thia-17,18,19,20-tetranor-5-prostenoic acid p-benzoylaminophenyl ester was obtained.

Analogously to Example 84, by the reaction of the mixed anhydride prepared from 9α,11α,15-trihydroxy-16-m-chlorophenoxy-13-thia-17,18,19,20-tetranor-5-prostenoic acid and isobutyl formate with the corresponding phenol of formula VII, the compounds of the formula I given in the following Examples 85 to 92 are preparable:

| Example | Compound of the formula I |
|---|---|
| 85 | 9α,11α,15-trihydroxy-16-m-chlorophenoxy-13-thia-17,18,19,20-tetranor-5-prostenoic acid p-acetylaminophenyl ester |
| 86 | 9α,11α,15-trihydroxy-16-m-chlorophenoxy-13-thia-17,18,19,20-tetranor-5-prostenoic acid p-(p-acetylaminobenzoylamino)-phenyl ester |
| 87 | 9α,11α,15-trihydroxy-16-m-chlorophenoxy-13-thia-17,18,19,20-tetranor-5-prostenoic acid p-(p-benzoylaminobenzoylamino)-phenyl ester |
| 88 | 9α,11α,15-trihydroxy-16-m-chlorophenoxy-13-thia-17,18,19,20-tetranor-5-prostenoic acid p-ureidophenyl ester |
| 89 | 9α,11α,15-trihydroxy-16-m-chlorophenoxy-13-thia-17,18,19,20-tetranor-5-prostenoic acid p-(3-phenylureido)-phenyl ester |
| 90 | 9α,11α,15-trihydroxy-16-m-chlorophenoxy-13-thia-17,18,19,20-tetranor-5-prostenoic acid (4-acetylamino-1-naphthyl) ester |
| 91 | 9α,11α,15-trihydroxy-16-m-chlorophenoxy-13-thia-17,18,19,20-tetranor-5-prostenoic acid (4-benzoylamino-1-naphthyl) ester |
| 92 | 9α,11α,15-trihydroxy-16-m-chlorophenoxy-13-thia-17,18,19,20-tetranor-5-prostenoic acid (4-ureido-1-naphthyl) ester |

EXAMPLE 93

The bromide of 5-triphenylphosphoniopentanoic acid p-benzoylaminophenyl ester used in Example 83 was prepared as follows:

(a) A mixture of 9 g. of 5-bromopentanoic acid, 10.2 g. of dicyclohexyl carbodiimide and 10.75 g. of p-benzoylaminophenol was boiled for 2 hours in benzene. After cooling, the solution was filtered and the solvent distilled off. As a residue 5-bromopentanoic acid p-benzoylaminophenyl ester was obtained.

The following esters are preparable analogously by reaction of 5-bromopentanoic acid with the corresponding phenol of formula VI:

5-bromopentanoic acid p-acetylaminophenyl ester,
5-bromopentanoic acid p-ureidophenyl ester,
5-bromopentanoic acid p-(p-acetylaminobenzoylamino)phenyl ester,
5-bromopentanoic acid p-(p-benzoylaminobenzoylamino)phenyl ester,
5-bromopentanoic acid p-(3-phenylureido)-phenyl ester,
5-bromopentanoic acid (4-acetylamino-1-naphthyl) ester,
5-bromopentanoic acid (4-benzoylamino-1-naphthyl) ester,
5-bromopentanoic acid (4-ureido-1-naphthyl) ester.

(b) 3.78 g. of 5-bromopentanoic acid p-benzoylaminophenyl ester and 2.7 g. of triphenylphosphine were boiled for 36 hours in 50 ml. of benzene. The solvent was distilled off. The bromide of 5-triphenylphosphoniopentanoic acid p-benzoylaminophenyl ester was obtained as a residue.

By reaction of the other 5-bromopentanoic acid esters mentioned in Example 93a with triphenyl phosphine, there are obtainable analogously the bromides of the following compounds:

5-triphenylphosphoniopentanoic acid p-acetylaminophenyl ester,
5-triphenylphosphoniopentanoic acid p-ureidophenyl ester,
5-triphenylphosphoniopentanoic acid p-(p-acetylaminobenzoylamino)-phenyl ester, 5-triphenylphosphoniopentanoic acid p-(p-benzoylaminobenzoylamino)-phenyl ester,
5-triphenylphosphoniopentanoic acid p-(3-phenylureido)phenyl ester,
5-triphenylphosphoniopentanoic acid (4-acetylamino-1naphthyl) ester,
5-triphenylphosphoniopentanoic acid (4-benzoylamino-1naphthyl) ester and
5-triphenylphosphoniopentanoic acid (4-ureido-1-naphthyl) ester.

EXAMPLE 94

0.25 g. of 9,15-dihydroxy-15-methyl-11-tetrahydropyranyloxy-13-thia-5-prostenoic acid p-benzoylaminophenyl ester (obtainable by the reaction of 2-(2-hydroxy-2-methylheptylthio)-5-hydroxy-3-tetrahydropyranyloxy-acetaldehyde lactol with triphenylphosphoniopentanoic acid p-benzoylaminophenyl ester in the presence of 2 moles of NaH) is stirred for 5 hours at 45° C. in 7 ml. of a mixture of acetic acid, THF and water (3:1:1). The solvent is distilled off, and after chromatographic purification of the residue (silica gel/ethyl acetate), 9,11,15-trihydroxy-15-methyl-13-thia-5-prostenoic acid p-benzoylaminophenyl ester is obtained.

EXAMPLE 95

This example describes the preparation of the most important compounds of formula III:

(a) 20 g. of a 20% sodium hydride dispersion in paraffin oil are washed three times with 30 ml. of dry n-pentane. The solvent is removed and 33 g. of trimethylsulphoxonium iodide is added thereto. 10 ml. of dimethyl sulphoxide are then added and the solution stirred for 20 minutes at room temperature until the gas evolution ceases. A solution of 14.2 g. of 2-heptanone in 15 ml. of dimethyl sulphoxide is dropwise added thereto. It is stirred for a further 2 hours. With ice cooling, 500 ml. of water is added thereto. The product is extracted three times with 250 ml. amounts of ether. The combined ether extracts are washed with water and dried with sodium sulphate. The solvent is distilled off and, after fractionation of the residue, 2-methyl-2-pentyloxirane is obtained as a colorless liquid; b.p.=55° C. (20 mm. Hg).

By reaction of the corresponding carbonyl compounds $R^2COR^3$ with trimethylsulphoxonium iodide in the presence of NaH, the following oxiranes are obtainable analogously:
2-pentyloxirane,
2-(1-methylpentyl)-oxirane,
2-(1,1-dimethylpentyl)-oxirane,
2-methyl-2-(1-methylpentyl)-oxirane,
2-(2-phenylethyl)-oxirane,
2-methyl-(2-phenylethyl)-oxirane,
2-(2-m-chlorophenylethyl)-oxirane,
2-(2-m-chlorophenylethyl)-2-methyl-oxirane,
2-methyl-2-(2-m-trifluoromethylphenylethyl)-oxirane,
2-(2-m-trifluoromethylphenylethyl))-oxirane,
2-phenoxymethyl-oxirane,
2-methyl-2-phenoxymethyl-oxirane,
2-m-chlorophenoxymethyl-oxirane,
2-m-chlorophenoxymethyl-2-methyl-oxirane,
2-m-methoxyphenoxymethyl-oxirane,
2-m-methoxyphenoxymethyl-2-methyl-oxirane,
2-m-trifluoromethylphenoxymethyl-oxirane, and
2-methyl-2-m-trifluoromethylphenxoymethyl-oxirane.

(b) Hydrogen sulphide is passed into 150 ml. of methanol with ice cooling, until the weight increase amounts to 3.2 g. A solution of 370 mg. of diethylamine in 11 ml. of methanol is added thereto, followed by 4.8 g. of 2-methyl-2-pentyloxirane in 18 ml. of methanol. Hydrogen sulphide gas again is passed into the solution for 15 minutes and the solution is permitted to stand for 12 hours at room temperature. The solvent is distilled off and the residue dissolved in 50 ml. of petroleum ether (b.p.=50°-70° C.), washed with water and dried with sodium sulphate. The solvent is distilled off and 2-hydroxy-2-methyl-heptanethiol is obtained as a colorless residual liquid.

IR: 920, 1140, 1380, 1465, 2570 and 3450 cm$^{-1}$;
NMR: signals at 0.96 ppm, 1.26 ppm, 2.27 ppm and 2.67 ppm.

By reaction of the other oxiranes mentioned in Example 95a with H$_2$S, the following thiols of formula III are obtainable analogously:
2-hydroxyheptanethiol,
2-hydroxy-3-methylheptanethiol,
3,3-dimethyl-2-hydroxyheptanethiol,
2,3-dimethyl-2-hydroxyheptanethiol,
2-hydroxy-4-phenylbutanethiol,
2-hydroxy-2-methyl-4-phenylbutanethiol,
4-m-chlorophenyl-2-hydroxybutanethiol,
4-m-chlorophenyl-2-hydroxy-2-methylbutanethiol,
2-hydroxy-4-m-trifluoromethylphenylbutanethiol,
2-hydroxy-2-methyl-4-m-trifluoromethylphenylbutanethiol,
2-hydroxy-3-phenoxypropanethiol,
2-hydroxy-2-methyl-3-phenoxypropanethiol,
3-m-chlorophenoxy-2-hydroxypropanethiol,
3-m-chlorophenoxy-2-hydroxy-2-methylpropanethiol,
2-hydroxy-3-m-methoxyphenoxypropanethiol,
2-hydroxy-3-m-methoxyphenoxy-2-methylpropanethiol,
2-hydroxy-3-m-triluoromethylphenoxypropanethiol, and
2-hydroxy-2-methyl-3-m-trifluoromethylphenoxypropanethiol.

The following Examples concern mixtures of compounds of the formula I with carrier or adjuvant materials which are conventional in pharmacy and which can be used, in particular, as pharmaceuticals:

EXAMPLE A

Tablets

A mixture, consisting of 30 g. of 11α,15-dihydroxy15-methyl-9-oxo-13-thiaprostanoic acid p-benzoylaminophenyl ester, 50 g. of lactose, 16 g. of maize starch, 2 g. of cellulose powder and 2 g. of magnesium stearate, were pressed into tablets using conventional procedures such that each tablet contained 10 mg. of of the active material.

EXAMPLE B

Dragees

Analogously to Example A, tablets were pressed and subsequently coated by conventional techniques with a coating consisting of sugar, maize starch, talc and tragacanth.

Tablets and dragees are obtainable analogously which contain one or more of the other active materials of formula I.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modification of the invention to adapt it to various usages and conditions.

What is claimed is:

1. Compounds of the formula

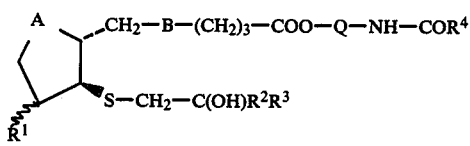

wherein A is —CO— or —CHOH—; B is —CH$_2$CH$_2$— or —CH=CH—; Q is 1,4-phenylene or 1,4-naphthylene; R$^1$ is H or OH; R$^2$ is H or CH$_3$; R$^3$ is alkyl of 1–8 carbon atoms or alkyl of 1–8 carbon atoms substituted by (a) phenyl, (b) phenyl substituted by at least one of CH$_3$, F, Cl, Br, OH, OCH$_3$ or CF$_3$, (c) phenoxy or (d) phenoxy substituted by at least one of CH$_3$, F, Cl, Br, OH, OCH$_3$ or CF$_3$; and R$^4$ is NH$_2$, CH$_3$, phenyl, p-acetylaminophenyl, p-benzoylaminophenyl or phenylamino.

2. The compounds of claim 1, wherein R$^1$ is OH.

3. The compounds of claim 1, wherein R$^3$ is a straight chain alkyl group of 4–7 carbon atoms.

4. The compounds of claim 1, wherein R$^3$ is alkyl of 1 or 2 carbon atoms substituted by phenyl or phenoxy, either of which is monosubstituted in the m- or p-position.

5. The compounds of claim 1, wherein Q is 1,4-phenylene.

6. The compounds of claim 1, wherein R$^4$ is CH$_3$, NH$_2$, 4-acetylaminophenyl or phenyl.

7. 11α,15-Dihydroxy-15-methyl-9-oxo-13-thiaprostanoic acid (4-benzoylaminophenyl ester), a compound of claim 1.

8. 11α,15α-Dihydroxy-9-oxo-13-thiaprostanoic acid (4-benzoylaminophenyl ester), a compound of claim 1.

9. A pharmaceutical composition which comprises an amount of a compound of claim 1 effective for lowering blood pressure and a pharmaceutically acceptable carrier, adjuvant or mixture thereof.

10. A method of lowering blood pressure in mammals which comprises administering an amount of a compound of claim 1 effective for lowering blood pressure.

11. The compounds of claim 1 wherein R$^1$ is OH; R$^3$ is a straight chain alkyl group of 4–7 carbon atoms; and Q is 1,4-phenylene.

* * * * *